United States Patent [19]

Harandi et al.

[11] Patent Number: 4,939,314

[45] Date of Patent: Jul. 3, 1990

[54] METHOD FOR ON-STREAM LOW-PRESSURE REGENERATION OF AN OLIGOMERIZATION CATALYST FROM A FLUID-BED REACTOR OPERATING AT HIGH PRESSURE WITH HYDROCARBONS IN A NON-LIQUID PHASE

[75] Inventors: Mohsen N. Harandi, Lawrenceville; Hartley Owen, Belle Mead, both of N.J.

[73] Assignee: Mobil Oil Corporation, New York, N.Y.

[21] Appl. No.: 286,204

[22] Filed: Dec. 19, 1988

[51] Int. Cl.$^5$ .............................................. C07C 2/12
[52] U.S. Cl. ...................................... 585/533; 502/41
[58] Field of Search ............... 585/533, 522, 570, 520; 502/41

[56] References Cited

U.S. PATENT DOCUMENTS

| | | | |
|---|---|---|---|
| 2,370,234 | 2/1945 | Degnen et al. | 23/288 |
| 2,688,195 | 9/1954 | Hyer | 34/57 |
| 2,833,699 | 5/1958 | Dix | 208/150 |
| 2,854,161 | 9/1958 | Payne et al. | 214/152 |
| 3,647,680 | 3/1972 | Greenwood et al. | 208/65 |
| 3,752,248 | 8/1973 | Greenwood et al. | 208/138 |
| 3,873,441 | 3/1975 | Jones | 208/166 |
| 4,400,493 | 8/1983 | Abernathy et al. | 585/520 |
| 4,487,985 | 12/1984 | Tabak | 585/577 |
| 4,576,712 | 3/1986 | Greenwood et al. | 208/138 |
| 4,615,792 | 10/1986 | Greenwood et al. | 208/134 |
| 4,665,250 | 5/1987 | Chu et al. | 585/533 |
| 4,746,762 | 5/1988 | Avidan et al. | 585/415 |
| 4,751,339 | 6/1988 | Beech, Jr. et al. | 585/533 |
| 4,777,316 | 10/1988 | Harandi et al. | 585/716 |
| 4,822,477 | 4/1989 | Avidan et al. | 208/49 |
| 4,827,069 | 5/1989 | Kushnerick | 585/333 |
| 4,851,602 | 7/1989 | Harandi et al. | 585/533 |

*Primary Examiner*—Anthony McFarlane
*Attorney, Agent, or Firm*—Alexander J. McKillop; Charles J. Speciale; L. G. Wise

[57] ABSTRACT

A process is disclosed for stripping and regenerating a zeolite catalyst at relatively low pressure compared to that of an oligomerization reactor operated with a turbulent fluid-bed at above about 515 kPa (60 psig). The reactor operates either with hydrocarbons in the gas phase, or, under near-critical or supercritical conditions, when they are in the super-dense phase. The super-dense phase exists outside a critical region in the phase envelope of the hydrocarbon mixture in the reactor, under conditions at which a liquid phase may not form (hence "non-liquid"). Whether the fluid-bed reactor is operated in the $C_5$-$C_{10}$ gasoline producing mode, the $C_{10}+$ distillate mode, or, the $C_{22}+$ lubes mode, continuous operation of a regenerator (for deactivated catalyst withdrawn from the reactor) at relatively low pressure, preferably less than 445 kPa (50 psig), is possible. A variable pressure "lock-stripper" recovers entrained hydrocarbon product from a recirculated catalyst stream before stripped catalyst is regenerated. Without the lock-hoppers, attrition of the catalyst would make the process uneconomical. Depending upon the process conditions, the oligomerized product is either $C_5$-$C_{10}$ gasoline, or a "heavies" stream (either distillate or lubes), with a minor proportion by weight of gasoline range hydrocarbons.

21 Claims, 4 Drawing Sheets

METHOD FOR ON-STREAM LOW-PRESSURE REGENERATION OF AN OLIGOMERIZATION CATALYST FROM A FLUID-BED REACTOR OPERATING AT HIGH PRESSURE WITH HYDROCARBONS IN A NON-LIQUID PHASE

BACKGROUND OF THE INVENTION

The oligomerization of olefins to higher hydrocarbons is a known process carried out with a zeolite oligomerization catalyst in a high pressure fluid bed reactor operating at oligomerization conditions of temperature and pressure. It was not known that the key to operating such a process economically was the ability to limit the deposition of coke in the reactor, allowing the withdrawal of a small slipstream of catalyst (recirculated stream) from the reactor; and, using pressure-isolatable lock-hopper zones between the reactor and the regenerator, and again between the regenerator and the reactor. This invention teaches such a process carried out in a reactor operating above about 515 kPa (60 psig) in which process the improvement comprises, depressurizing (or 'depressurizing') and purging the recirculating ('recirc' for brevity) stream, stripping and regenerating it at less than about one-half the reactor operating pressure, and repressuring ('pressurizing') it to a pressure sufficient to return it to the reactor, using lock-hopper zones. The terms 'depressuring' and 'pressurizing' are used hereinafter because they are phonetically distinct.

Lower olefins in the feed are converted to heavier hydrocarbons ("heavies") in a single-zone fluid-bed reactor, operating at pressure and temperature conditions at which no liquid hydrocarbon phase is present, hence referred to as a "non-liquid phase". This non-liquid phase may be the gas phase, or one which is "super-dense", referred to as such, because the pressure is so high as to maintain the hydrocarbons in the fluid bed under near-critical or supercritical conditions. The term "super-dense phase" is not to be confused with the common usage of the term "dense phase" as typically applied to a fluidized bed of catalyst, but refers to the mixture of hydrocarbons at or above $P_{max}$ (defined herebelow) in the reactor. The particular conditions of operation of our process depend upon whether the fluid bed operates with hydrocarbons in the gas phase; or, operates in the super-dense phase, either of which is referred to as non-liquid. Operation of the reactor in the non-liquid phase is a preferred embodiment of this invention.

Feed to the reactor is introduced at the bottom, in an amount sufficient to fluidize the bed; the recirc stream, containing used (mostly deactivated) catalyst is withdrawn from the reactor and stripped, then regenerated and returned to the fluid bed. The oligomerized product leaves from the top of the reactor so that the relative direction of flow of catalyst and feed is typical of that in a fluid bed operating in the turbulent regime.

When the reactor is used to oligomerize olefins to gasoline, it is referred to as a MOG (Mobil Olefin to Gasoline) reactor operating in the gasoline mode; when used to oligomerize olefins to distillate, the reactor is referred to as a MOD (Mobil Olefin to Distillate) reactor operating in the distillate mode; when used to oligomerize olefins to lubes, the reactor is referred to as a MOL (Mobil Olefin to Lubes) reactor operating in the lubes mode; and, the reactor is referred to as a MOGDL reactor when it may be used to discharge any of the foregoing functions.

Operation of the MOG reactor in the gas phase under sub-critical pressure, is described in greater detail in our U.S. Pat. No. 4,777,316 issued Oct. 11, 1988 and in copending application Ser. No. 197,543 of Johnson D. and Avidan A. filed on May 23, 1988, the disclosures of which are incorporated by reference thereto as if fully set forth herein. In the "gas-phase" embodiment of our invention, operation of the reactor ensures that the reaction occurs in the gas phase, at conditions of pressure and temperature which are (1) below both $P_{max}$ and $T_{max}$; or (2) below $P_{max}$ but above $T_{max}$. In the "super-dense" embodiment of our invention, the operation of the reactor ensures that the reaction occurs in the super-dense phase requiring conditions of pressure and temperature which are (3) at or above both $P_{max}$ and $T_{max}$, so that in all instances, the reaction occurs outside the phase envelope, as described in greater detail in our copending patent application Ser. No. 184,465 filed Apr. 20, 1988 the disclosure of which is incorporated by reference thereto as if fully set forth herein.

By sub-critical pressure we refer to a pressure below $P_{cr}$; and by "near-critical" conditions we refer to a pressure $P_{max}$ at or above which no liquid may be present, this pressure typically being not less than about 344.5 kPa (50 psia) below the critical pressure $P_{cr}$. By sub-critical temperature we refer to a temperature below $T_{cr}$ but also below $T_{max}$, at or above which no liquid may be present. The precise $P_{max}$ and $T_{max}$ for a particular feedstock will vary depending upon its composition. For a typical, predominantly $C_3-C_4$ light gas, $P_{max}$ is about 4000 kPa (565 psig) and $T_{max}$ is about 132° C. (270° F.). By "super-critical" conditions we refer to conditions above $P_{cr}$, $T_{cr}$ for the product, and outside the "envelope" of the phase diagram. By "the phase diagram", we refer in all cases to the phase diagram for all the hydrocarbons present in the reactor at any moment.

Since our process is an exothermic process, most economically practiced with the reactor operating continuously, it is necessary to regenerate the catalyst, either continuously or semi-continuously, in a continuous process. By "continuous process" we refer to the reactor operating continuously. In such a process, the regenerator may operate semicontinuously, or, continuously, as will be explained hereinafter. Because the reactor operates at relatively high pressure with the hydrocarbons in the non-liquid phase, a practical process presents a peculiar set of problems which are exacerbated when operation is at near-critical, and typically, super-critical pressure and temperature. This invention relates to an ingenious and unobvious solution to problems associated with the non-liquid phase, whether the gas phase, or, the super-dense phase, at a pressure often well above about 650 kPa (80 psig).

As one skilled in art will appreciate, the mass of hydrocarbons in the non-liquid phase associated with the withdrawn catalyst is high because of the high pressure, and one must strip this mass from the catalyst before it is oxidatively regenerated in a regenerator. Since a prerequisite for stripping is high volumetric flow of stripping gas, it is economically out of the question to strip with an inert gas at elevated pressures, especially when the reactor operates above $P_{max}$ which is typically above about 2410 kPa (335 psig), and particularly uneconomical at or above about 6300 kPa (900 psig).

Practical stripping requires it be done at relatively low pressure to derive a double-barreled benefit, both from a decrease in pressure, and from a high volumetric flow of a suitably economical stripping medium such as steam, at relatively low pressure. The precise low pressure at which stripping is to be effected is determined by the economics of the process, but for obvious reasons, will be the highest pressure at which stripping is economical. Except that, though steam is most convenient and economical, the zeolite oligomerization catalyst is highly sensitive to a high partial pressure of steam, which high partial pressure tends to deactivate the catalyst. This consideration militates against using steam except at a suitably low partial pressure.

Stripping a stream of catalyst withdrawn from a fluidized bed of catalyst is routinely done in a fluid catalytic cracker (FCC) with a number of variations of old techniques taught for example in U.S. Pat. No. 2,688,195 (class 34/57) and U.S. Pat. No. 2,833,699 (class 208/150). In the latter, steam jet blasts catalyst as it enters the stripping zone, followed by contacting the catalyst as a dense-phase fluidized bed. How to drop the pressure in the stripping zone, whether by a factor of two or more, is not a technical issue in the prior art, since the operation of the FCC reactor is never substantially above atmospheric, being usually below about 50 psig. Moreover, there is generally no problem in the prior art, with respect to coping with a sudden, large change of pressure after the hydrocarbons are withdrawn, or with a transition of phases they might undergo. They are always in the vapor phase, well below either $P_{cr}$ or $P_{max}$, and usually well above either $T_{cr}$ or $T_{max}$.

Still further, the entire bed of catalyst in a FCC reactor is stripped several times within an hour so that the rate of withdrawal of catalyst for stripping and regeneration is at least 50% of the bed per hr. The volumetric flow of stripping steam required is determined by the flow rate of the withdrawn catalyst, not the pressure in the reactor, so that the mass flow of steam relative to the withdrawn catalyst is low, determined by the reactor pressure. Thus the reactor pressure is only an incidental, rather than a critical factor, in the cost of stripping steam. Since in the teaching of the prior art there is no serious economic penalty related to the volumetric and mass flow of stripping steam to be used, no serious threat of deactivation due to excessive steam partial pressure, and no danger of forming a liquid under such conditions, the considerations relating to the problem of stripping and regenerating a FCC catalyst, then returning it to the FCC reactor, have little in common with those encountered in our process.

As one skilled in the art will also appreciate, a zeolite oligomerization catalyst must be regenerated at relatively low oxygen concentration to minimize catalyst deactivation, and regeneration is typically done by recirculating regenerator flue gas. To maintain required fluidization velocity through the regenerator, a high volumetric flow of oxygen-containing gas, whether air or flue gas, is also demanded. This demand cannot be met economically if regeneration is to be done at high pressure.

In each operation, namely stripping and regeneration, to maintain a sufficiently high volumetric flow ($m^3$/min, or $ft^3$/min) of stripping gas, an increase of operating pressure predetermines a correspondingly high mass flow (kilos/hr or pounds/hr) of gas. Aside from the fact that higher operating pressures require that stripping gas and regenerating gas be each compressed to the required high pressures at considerable cost for power, this second consideration of required volumetric flow, along with the first, relating to steam deactivation, determines that the efficacy of both stripping and regeneration will be adversely affected as pressure increases. Particularly as the cost of purchasing and operating a compressor tends to increase exponentially as its capacity and output pressure increases above about 100 psig, it is necessary, for economy, to operate with as low a pressure as will yield the desired process results.

Notwithstanding a desirably low superatmospheric operating pressure effective for the oligomerization reaction chosen, circulation of the catalyst through valves under conditions which dictate a substantial pressure drop, cause excessive attrition of the catalyst. It is fortuitous that the use of lock-hoppers permits control of the pressure drop from one stage to another such that deleterious attrition of the catalyst is minimized. The lock-hoppers also permit operation of the regenerator at as low a pressure as the other process conditions of its economical operation permit.

The unique feature of being able to operate this process with a low "coke-make" allows regenerating a very small fraction of the reactor inventory semicontinuously, which in turn may make a presently, otherwise typically uneconomical and unattractive process, attractive. This invention relates to a surprisingly effective and commercially significant solution to problems relating to stripping and regenerating the catalyst by adapting a system for "stepping down" the spent catalyst pressure to a low pressure, preferably about 50 psig, sufficient for adequate stripping, and then regenerating the catalyst at an even lower pressure.

Though for neither of the foregoing reasons, the concept of isolating the reactor and the regenerator from one another, was taught in U.S. Pat. No. 2,370,234 to Degnen et al (class 23/288) nearly fifty years ago, and in U.S. Pat. No. 2,854,161 to Payne (class 214/152); and, stepping down the reactor pressure for stripping and regenerating the catalyst has been used in numerous modifications of moving-bed processes. Continuous low pressure naphtha reforming is taught in U.S. Pat. No. 3,647,680 (class 208/65) and U.S. Pat. No. 3,752,348 (class 208/138) to Greenwood et al.; and U.S. Pat. No. 3,873,441 to Jones (class 208/166) teaches how to cope with the problems of withdrawing a mixed-liquid/gas-phase hydroprocessing catalyst from a high pressure reactor. More recently lock-hoppers have been used in moving bed catalytic reforming processes disclosed in U.S. Pat. No. 4,576,712 to Greenwood (class 208/138) and U.S. Pat. No. 4,615,792 (class 208/134). We know of no suggestion in the prior art to use a lock-hopper to transport spent zeolite catalyst from a fixed turbulent fluid bed reactor, to a fixed turbulent fluid bed regenerator via a pressure-isolatable zone and a stripper in which the catalyst could be effectively stripped.

None of the teachings of the foregoing references is reasonably applicable to solving the problems of our process because the problems we encounter arise under different technical circumstances. The solution to our problems is made possible only because of a peculiar set of circumstances. The zeolite catalyst used, such as a ZSM-5 type catalyst is especially well-adapted for use in high pressure reactors, but because of operation at such high pressure it has a high percent by weight (% by wt) of hydrocarbons in the voids and pores of the catalyst. Yet it should, and can be stripped quickly. If steam is chosen as the stripping medium, the catalyst can withstand exposure to steam provided the partial pressure of steam is not too high, because the higher the temperature and/or the partial pressure of steam, the greater the deactivation. Stripping and regeneration is quick because of the very low rate of coking of the catalyst, generally less than 1% by wt, and typically less than 0.4% by wt of the olefins charged, which low rate in turn permits a correspondingly low rate of withdrawal of the recycle stream. The unexpectedly low catalyst circulation rate makes the costs of depressuring/pressurizing affordable and ideally suited for this process.

SUMMARY OF THE INVENTION

A process has been discovered for efficiently regenerating a recirculated slipstream of catalyst ('recirc stream' for brevity) withdrawn from a fluid bed oligomerization reactor operating at high pressure, from which reactor the recirc stream comprising used catalyst and sorbed hydrocarbons is flowed to a pressure-reducing, first pressure-isolatable transfer zone ('purging zone') provided by a lock-hopper means ('purging lock-hopper), then into a stripping zone to strip away the hydrocarbons from recirc catalyst in the recirc stream; optionally, the purging lock-hopper and stripper are replaced with a unitary pressure-isolatable lock-stripper means ('lock-stripper'); the recirc catalyst is stripped with a stripping gas, for example steam or nitrogen at a lower pressure than the reactor, and regenerated at an even lower pressure than the stripper before the recirc catalyst is pressurized in a pressure-increasing, second pressurizable transfer zone ('charging zone') such as another lock-hopper means ('charging lockhopper'), and flowed back to the reactor to be mixed with catalyst in the reactor ('reactor catalyst') for reuse. Using lock-hoppers avoids excessive attrition of the catalyst.

It is therefore a general object of this invention to provide an effective on-stream stripping and regenerating scheme, for an olefin oligomerization process, carried out in a fixed turbulent fluid bed from which a recirc stream of spent zeolite catalyst particles is withdrawn, stripped, regenerated and returned to the reactor's oligomerization zone, comprising, (a) withdrawing less than 30 percent by weight of reactor catalyst per hour in said recirc stream in which said catalyst has less than 1% by weight of coke deposited on it (based on the weight/hr of olefins fed), and is fluidized by hydrocarbons in a non-liquid phase at above about 650 kPa (80 psig);

(b) confining the recirc stream in a pressure-isolatable purging zone and depressuring it to below about 50% of the reactor pressure to purge a major proportion by weight of the hydrocarbons in said stream;

(c) transferring purged catalyst from said purging zone to a stripping zone;

(d) stripping said purged catalyst with a stripping medium to produce a stripped catalyst;

(e) oxidatively regenerating the stripped catalyst to produce a regenerated catalyst essentially free of deposited coke; and, (f) returning said regenerated catalyst to the oligomerization zone via a pressure-isolatable charging zone, pressurizable to a pressure greater than the operating pressure of the oligomerization zone, whereby, without interrupting on-stream operation of the reactor, stripping and regenerating the recirc catalyst may be effected semi-continuously, or, when "swing" lock-hopper zones are used, continuously.

It is another general object of this invention to provide an olefin oligomerization process analogous to that described hereinabove, except that steps (b) and (c) are substituted by a single, variable pressure step of stripping the recirc catalyst stream in a lock-stripping zone which is initially at a pressure sufficiently high to avoid sonic flow of catalyst through the line from the reactor to the lock-stripper, and in which the pressure is progressively reduced to just above that of the regenerator, to enable transfer of the catalyst thereto.

It is a specific object of this invention to provide the foregoing process for a MOGDL reactor operating at sufficiently high pressure and temperature to oligomerize olefins in a light gas or light naphtha feedstream under super-dense conditions, comprising, (a) flowing recirc catalyst in an amount less than 10% by wt per hour of the reactor catalyst inventory, with sorbed hydrocarbons, from said reaction zone which is at or above $P_{max}$ and $T_{max}$, into a pressure-isolatable purging zone, (b) venting said purging zone and separating the catalyst to recover purged hydrocarbons, and to reduce pressure over the purged catalyst, preferably to less than about 375 kPa (40 psig), (c) flowing purged catalyst from said purging zone to a stripping zone at a temperature in the range above about 204° C. (400° F.) but below a temperature deleterious to said catalyst, in which stripping zone the purged catalyst in a fluidized state is stripped of said hydrocarbons with a stripping gas to provide stripped catalyst, (d) flowing said stripped catalyst to a regeneration zone in which a fluid bed operates at a pressure above atmospheric but lower than about 50 psig, (e) introducing into said regeneration zone an oxygen-containing gas in an amount sufficient to regenerate said stripped catalyst at a temperature in the range from above about 371° C. (700° F.) but below a temperature deleterious to said catalyst, so as to provide regenerated catalyst, (f) flowing the regenerated catalyst to a pressure-isolatable charging zone, (g) pressurizing said charging zone with said feed in the superdense phase to a pressure above the operating pressure of said reactor, and, (h) returning said regenerated recirc catalyst from said charging zone to said reactor.

It is also a specific object of this invention to provide the stripping and regeneration process under super-dense conditions, described hereinabove, except that steps (b) and (c) are substituted by a single, variable-pressure step of stripping the recirc catalyst stream in a lock-stripping zone which is initially at a pressure sufficiently high to avoid sonic flow of catalyst through the line to the lock-stripper, and is progressively reduced to a pressure just above that of the regenerator.

BRIEF DESCRIPTION OF THE DRAWING

The foregoing and other objects and advantages of our invention will appear more fully from the following description, made in connection with the accompanying drawings of a preferred embodiment of the invention, wherein.

DETAILED DESCRIPTION OF PREFERRED EMBODIMENTS

The efficacy of our process derives from the unexpectedly low coke formation and low rate of recirculation of catalyst required; which, in turn allows lock-hoppers to be used to add recirc catalyst to, and to remove it from the MOGDL oligomerization reactor, allowing the quick purging and stripping of a non-liquid hydrocarbon phase carried by recirc catalyst withdrawn from the MOGDL reactor. The lock-hoppers allow transfer of catalyst from one processing stage to another, with a sufficiently low pressure differential as to allow a tolerable level of attrition of the catalyst. A lock-hopper means is conventionally used to make a transition from a high-pressure zone to one at lower pressure in those instances where a pressure-reducing valve is inapt. A lock-hopper type device comprises a vessel of adequate volume in selectively open or closed communication with another vessel.

In one (first) embodiment of our process, the recirculated catalyst ('recirc' catalyst for brevity) withdrawn from the MOGDL reactor is transferred to the purging lock-hopper, depressured to purge volatile hydrocarbons from the catalyst, then flowed to a stripper where the purged catalyst is stripped at a temperature not substantially very different from that in the reactor, but at a pressure preferably less than one-half that in the reactor; then the stripped catalyst is oxidatively regenerated at a temperature in the range from about 371° C.-510° C. (700° F.-950° F.), stripping and regeneration being done while the recirc catalyst is in the fluidized state at superatmospheric pressure below about 100 psig, preferably below about 50 psig; and, the regenerated recirc catalyst is finally returned under pressure through the charging lock-hopper, to the reactor while it remains on-stream.

In another (second) embodiment, the function of the purging lock-hopper is preempted by a stripper which also provides the function of a purging lock-hopper (hence referred to as a "lock-stripper").

By "volatile" hydrocarbons we refer to those which are released in the gas phase from the recirc catalyst, it being recognized that a minor proportion, less than 45% by volume, and preferably about 10% by vol of the hydrocarbons withdrawn in the recirc stream, will remain sorbed in the catalyst at the reduced pressure.

Figure 4:
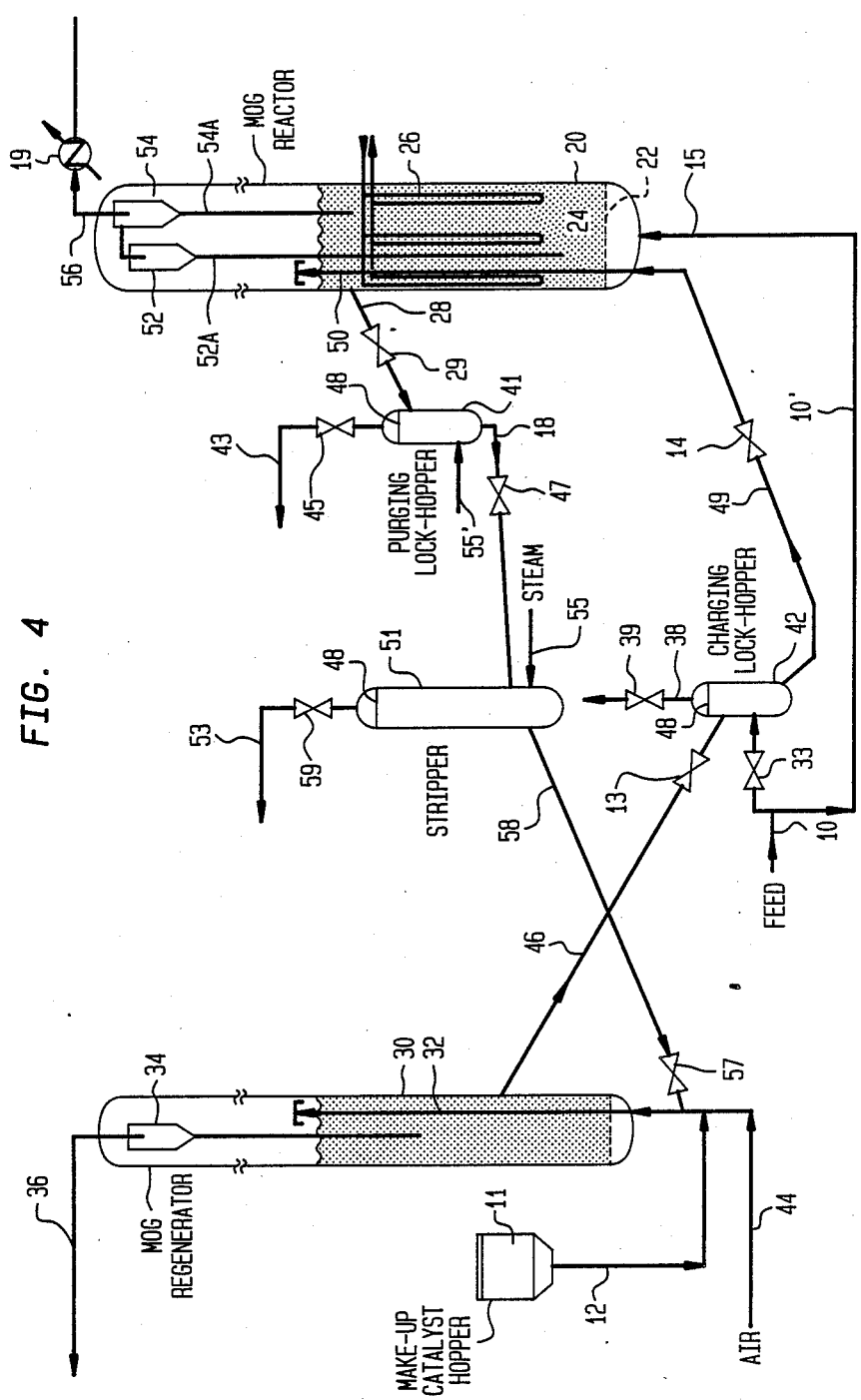
FIG. 4 is a flow diagram for the MOG process (that is, operating in the MOG mode) in which light gas or light naphtha is converted to gasoline, schematically illustrating the operational relationship of a MOG fluid bed reactor, a fluid bed oligomerization regenerator (also referred to as a MOG regenerator, in the MOG mode), a stripper, a purging lock-hopper intermediate the reactor and the MOG regenerator, and a charging lock-hopper intermediate the MOG regenerator and the reactor. Coked up catalyst is oxidatively regenerated in a MOG regeneration zone, either periodically, or continuously, and flowed to the charging lock-hopper from which it is charged to a oligomerization zone. As illustrated, the stripping is not continuous because a single purging lock-hopper is used; with an additional "swing" purging lock-hopper, catalyst to be regenerated may be continuously stripped and flowed to the regeneration zone; and, with an additional "swing" charging lock-hopper, catalyst may be continuously charged to the oligomerization zone.

In the schematic flowsheet of the first embodiment, illustrated in FIG. 4, the feedstream 10 is processed through a single MOGDL reactor 20, a regenerator 30, a stripper 51 intermediate the reactor and regenerator, and a pair of appropriately valved lock-hoppers the first (referred to as the 'purging lock-hopper' 41) upstream of the stripper, the second (referred to as the 'charging lock-hopper' 42) downstream of the regenerator, into which charging lock-hopper, regenerated catalyst is flowed when the charging lock-hopper is isolated from the reactor. From the charging lock-hopper, the catalyst is flowed into the reactor when the charging lock-hopper is pressurized to a pressure greater than that of the reactor. Fresh catalyst may be introduced at any convenient location within the system.

Depending upon the particular mode of operation chosen for the reactor, that is whether in the sub-critical or super-critical phase, and whether in the gasoline (MOG), distillate (MOD) or lubes (MOL) modes, the catalytic oligomerization conditions are chosen within an appropriate range of temperature and pressure. Temperature is chosen in the range from about 204° C. (400° F.) to about 538° C. (1000° F.). Pressure is chosen in the range from about 650 kPa (80 psig) to about 13880 kPa (2000 psig), the higher the molecular weight of product desired, the higher the pressure and the lower the temperature. The reactor operates at a weight hourly space velocity ("WHSV" it being understood that WHSV signifies pounds of olefins fed per pound of zeolite per hour) in the range from about 0.1 to about 20 $hr^{-1}$, and a pentane to pentene ratio of less than 0.2 when the conversion of propene is at least 75%. Since the oligomerization reaction is exothermic, the fluid bed is typically cooled by internal cooling coils to maintain the temperature within a preselected range.

A state of the art MOG reactor using a crystalline zeolite, for example as in copending U.S. Pat. No. 4,746,762 to Avidan et al, uses a fluid bed to convert light gas, namely $C_2^+$ olefins, but predominantly $C_3$-$C_5$ olefins, or, light naphtha, into "heavies" in a single zone operating at sub-critical pressure to maximize the production of gasoline.

In a preferred embodiment, a $C_3$-$C_4$ olefin-rich light gas stream which may contain some higher olefins, ethylene (preferably less than 30% by wt), as much as 40% by wt of $C_4^-$ alkanes, and up to 20% by wt hydrogen, is upgraded to gasoline with better than 80% conversion of the olefins in a MOG reactor by catalytic conversion in a dense phase turbulent fluidized bed of solid acid ZSM-5 type of relatively low activity zeolite catalyst (average equilibrated alpha <15, preferably <5), as measured by a procedure analogous to that taught in U.S. Pat. Nos. 3,827,968 and 3,960,978 to Givens et al.) operating at a pressure below 1480 kPa (200 psig) in the absence of added hydrogen. The reactants and gasoline-range effluent are at sub-critical pressure but at relatively high temperature so that they are always in the gas phase.

In the most preferred embodiment a fluid bed MOG reactor operates with a relatively low activity, average equilibrated alpha >3, preferably from 5 to about 10, and the hydrocarbons are in the dense phase. The MODL reactor also operates as a fluid bed with the relatively low activity catalyst, but the hydrocarbons are in the super-dense phase. The effluent from MOD and MOL reactors are distillate-range and lubes-range products respectively, which products are condensed and recovered, as is the MOG effluent, preferably with a subsequent fractionation step to separate insufficiently oligomerized hydrocarbons from "inerts" not likely to be oligomerized. The oligomerizable hydrocarbons are recycled to the oligomerization reactor.

The MOG reactor is preferably operated in the gas phase, but the MODL fluid bed reactor is preferably operated at or above $P_{max}$ and $T_{max}$, conditions high enough to keep the reactants, and the effluent produced in the super-dense phase, yet, to avoid forming liquid in the reactor.

The particular operational mode of MOGDL reactor chosen, whether under gas phase, or super-dense phase conditions, depends upon the economics of operation for a particular feedstock available in the refinery, and other considerations which pertain to operation of fixed beds rather than a fluid bed. The particular operating conditions chosen for a specific mode depend upon what particular quality of gasoline, distillate or lubes is desired, and what minor amount of lower range hydrocarbons is acceptable in the product, for example, the content of $C_5$–$C_7$ hydrocarbons in the distillate.

Operation with a fluid bed MOG reactor (Gasoline Mode):

In our single zone fluid-bed MOG reactor it is economical to operate the MOG reactor in the gas phase, at an average equilibrated alpha in the range from about 1 to 20, relatively low WHSV in the range from about 0.1 to 20 hr$^{-1}$, a superficial velocity of about 0.15 m/sec to about 2 m/sec (0.5-6.5 ft/sec), a pressure below about 1825 kPa (250 psig), preferably in the range from about 1140 kPa (100 psig) to about 1480 kPa (200 psig), and a temperature in the range from about 204° C.-427° C. (400°-1000° F.), preferably 316° C. to 538° C. (600°-800° F.), which is maintained with a typical feed inlet temperature in the range 38°-204° C. (100°-400° F.) to convert at least 50% of the olefins to $C_5$+ components at a weight ratio of $C_5$:$C_5^{=}$ <5.

Figure 1:
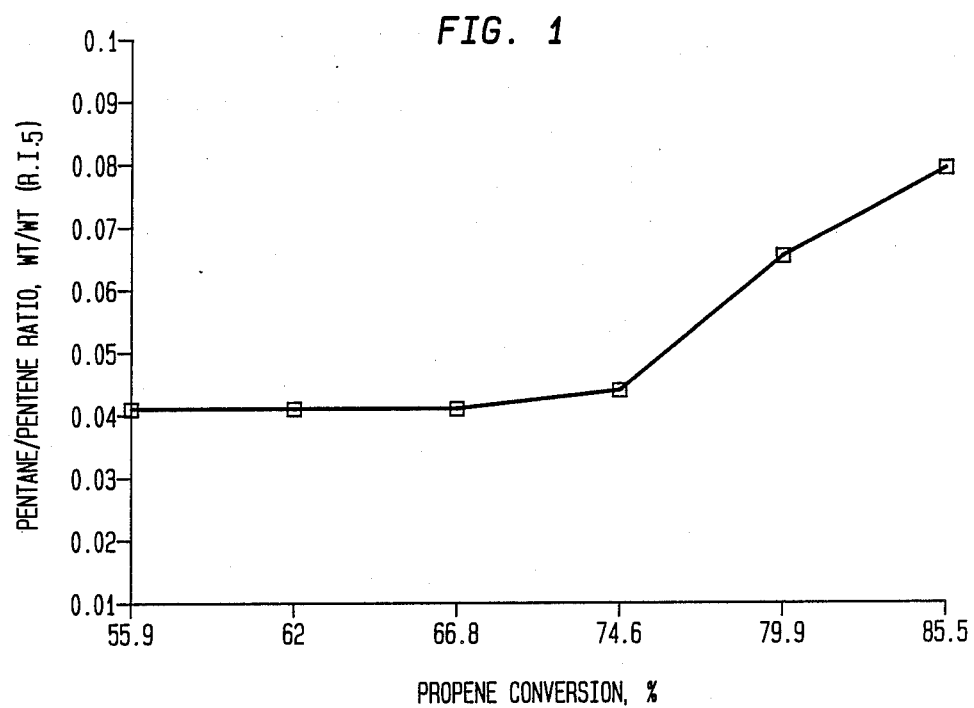
FIG. 1 is a linear plot showing propene conversion vs pentane/pentene ratio, wt/wt in the MOG reactor.

Operation under the foregoing gas phase conditions with the ZSM-type catalyst provides a controllable reaction severity index (R.I.). The R.I. is simply the ratio of alkane:alkene in the product, and is expressed herein as the ratio of $C_5$:$C_5^{=}$ in the effluent. It may also be expressed as the ratio of propane:propene, as for example in U.S. Pat. No. 4,547,616 to Avidan et al. Because we have defined R.I. with respect to pentane:pentene, we identify the ratio as "(R.I.)$_5$" and have so labelled it in FIG. 1 which illustrates the unique relationship of "(R.I.)$_5$" as a function of propene conversion in our MOG fluid bed. It is evident that at a propene conversion in the range from about 55% to 70%, the R.I. is about 0.04, and it is preferred to operate the MOG fluid bed with a R.I. in the range from about 0.5:1 to about 3:1.

The fluid-bed density in the MOG reactor which preferably operates to maximize the yield of gasoline range olefins under the foregoing conditions, is typically in the range exceeding 400 kg/m$^3$ (25 lb/ft$^3$), up to about 592 kg/m$^3$ (37 lb/ft$^3$), the higher the pressure, the higher the density of the gaseous phase, and the lower the bed density. The preferred particle density is preferably in the range from about 1.2-2.5 g/cc. A typical dense fluid bed has a minimum fluidization velocity of 0.014 m/sec (0.047 ft/sec). A turbulent fluid bed typically operates at a superficial velocity in the range from about 0.15-0.61 m/sec (0.5-2 ft/sec).

The weight of hydrocarbons (not coke, which is distinct from hydrocarbons) sorbed in the catalyst in the recirc stream withdrawn, will vary depending upon operating conditions, ranging from about 0.00045 kg (0.01 lb) to about 0.23 kg (0.5 lb) of hydrocarbons for 45.4 kg (100 lb) of the reactive components fed to the MOG reactor. The weight of hydrocarbons entrained in the recirc stream before it is stripped, is in the range from about 0.1 kg (0.25 lb) to about 4.54 kg (0.10 lb) per 45.4 kg (100 lb) of recirc catalyst. For example, with a feed rate of 18,160 kg/hr (40,000 lb/hr) having 1,226 kg/hr (27,000 lb/hr) reactive hydrocarbons, about 63.6 kg/hr (140 lb/hr) of coke is made with 22.7 kg (50 lb/hr) entrained hydrocarbons and a catalyst circulation rate of 1544 kg/hr (3400 lb/hr). Operation of the stripper will determine the amount of sorbed volatile hydrocarbons (not stripped) passing to the regenerator. It will be evident to one skilled in the art that as much of the hydrocarbons should be stripped in the stripper, at as low a pressure and with as much stripping gas, say steam, as is economically feasible.

The operation of the process with a MOG reactor comprises, (a) contacting light gas or light naphtha with a finely divided porous aluminosilicate catalyst having an average particle size in the range from about 20 microns to about 100 microns, a constraint index in the range from about 1 to about 12, and an operating alpha less than 10, preferably in the range from 0.5 to about 5, said catalyst maintained in a single zone turbulent regime MOG fluid-bed operating at a temperature in the range from about 204°-538° C. (400°-1000° F.) and a pressure in the range from about 650-2860 kPa (80-400 psig) in the absence of added hydrogen, (b) flowing said light gas or naphtha through said MOG bed at a weight hourly space velocity (WHSV) in the range from about 1 to about 30 hr$^{-1}$, and preferably from 0.5 to 5 hr$^{-1}$, with a superficial vapor velocity in the range from about 0.15-2 m/sec (0.5 ft/sec-6 ft/sec), (c) maintaining a content of catalyst fines in the range from about 10% to about 20% by wt, based on the weight of the catalyst in the MOG bed, said fines having a particle size less than 32 microns, (d) producing a MOG effluent containing a major amount of $C_5$+ hydrocarbons (pentanes, pentenes and heavier), essentially free of aromatics, and containing a minor amount of $C_4^{-}$ (butane, butenes and lighter);

(e) withdrawing less than 30 percent by weight of MOG reactor catalyst per hour in a recirculated stream from said fluid bed;

(f) confining the recirculated stream in a first pressure-isolatable transfer zone and depressuring it to below about 100 psig, preferably below 50 psig but superatmospheric, to purge a major proportion by weight of the hydrocarbons in the recirculated stream;

(g) transferring purged catalyst from said first pressure-isolatable transfer zone to a stripping zone;

(h) stripping said purged catalyst with a stripping medium to produce a stripped catalyst having coke deposited thereon in an amount less than 1%, preferably less than 0.4% by weight of the olefins charged to said fluid bed;

(i) oxidatively regenerating the stripped catalyst in a regeneration zone to produce a regenerated catalyst essentially free of carbon deposits;

(j) transferring regenerated catalyst from said regeneration zone to a second pressure-isolatable transfer zone; and, (k) returning said regenerated catalyst to the MOG reactor's oligomerization zone by pressurizing the second pressure-isolatable transfer zone to a pressure greater than the operating pressure of the oligomerization zone.

In the best mode, steps (f), (g) and (h) are replaced with a single stripping step in the lock-stripping zone. The lock stripper is pressurized with stripping medium to a pressure greater than one-half the pressure in the reactor, before the recirc catalyst is flowed into the lock-stripper, thus avoiding sonic velocity through the recirc catalyst valve as it is opened. The valve is then closed to isolate the lock-stripper and the pressure in the lock-stripper is then decreased to strip the sorbed hydrocarbons.

The hydrocarbon effluents from the purging lock-hopper, the charging lock-hopper and the stripper overhead, may be combined and filtered to remove catalyst fines, before the hydrocarbons are recycled to the process.

Operation with a fluid bed MOD reactor (Distillate Mode):

The MOD reactor is a fluid bed particularly adapted for the production of distillate, operated at or above $P_{max}$ and $T_{max}$, at which conditions it is critical that there be no liquid phase present. It is essential that the MOD reactor be operated in the super-dense phase above $P_{max}$ and $T_{max}$, of either the hydrocarbon feed, the oligomerized effluent, or any intermediate hydrocarbon formed during the reaction. In other words, operation requires that the pressure and temperature be maintained outside a critical region (critical P and T region) in the phase diagrams of either the feed, the product, or any intermediate. This critical P and T region is defined by an arc circumscribed around the critical point, between the vertical through the critical point, and, the dew point curve of the phase diagram, the arc having a radius corresponding to about 344.5 kPa (50 psia). The fluid bed MOD operates outside a tightly circumscribed critical P and T region which region lies near, or above the apex of a phase diagram defining the critical point ($P_{cr}$, $T_{cr}$) of the mixture of hydrocarbons in the reactor. The operating P and T conditions of the MOD reactor may be super-critical (that is, both are above $P_{cr}$, $T_{cr}$ of the mixture); or, only one or the other may be below $P_{cr}$, $T_{cr}$; or, both may be below $P_{cr}$, $T_{cr}$; provided they are not in the critical P and T region so that no liquid can form. Operation at precisely $P_{cr}$, $T_{cr}$ conditions, or too close to them (within the critical P and T region), involves too high a risk of formation of a liquid phase, and is therefore avoided.

The fluid-bed density in the MOD reactor operating to maximize the yield of distillate is in the range exceeding 300 kg/m$^3$ (18.7 lb/ft$^3$), up to about 850 kg/m$^3$ (53 lb/ft$^3$). The preferred particle density is preferably in the range from about 1.2–2.5 g/cc. A typical superdense fluid bed has a minimum fluidization velocity of 0.014 m/sec (0.047 ft/sec) and operates at a superficial velocity in the range from about 0.03–0.61 m/sec (0.1–2 ft/sec). The equilibrated activity of the catalyst is preferably in the range from about 2 to 15, and operation is at low severity, $(R.I.)_5 < 0.2$.

Since the MOD reactor, like the MOG reactor, is operated as a fluid bed in the turbulent regime, the content of catalyst fines is maintained in the range from about 5% to about 20% by wt, based on the weight of the catalyst in the MOD bed, the fines having a particle size less than 32 microns. Preferred operation of the fluid bed MOD reactor excludes a region circumscribed by about a 50 psia differential from $P_{cr}$, $T_{cr}$ of the hydrocarbon mixture in the bed, and bounded by the portion of the bubble-point/dew-point curve downwardly inclined from said point. Under such high pressure conditions, the reaction is prejudiced in favor of oligomerization with a minimum of cracking of heavy $C_{10}{}^+$ components, so that particular ranges of temperatures are found most desirable for a "make" in the desired distillate range. The precise optimum combination of pressure and temperatures, along with WHSV, for a particular catalyst, is best arrived at with such trial and error as one skilled in the art is enured to.

In a fluid-bed MOD reactor, the entire bed is in a fluid phase in which the solid acts both as catalyst and heat transfer sink. In this process, we regard the super-dense phase as being neither gas nor liquid, but for convenience and familiarity, we treat the oligomerization reaction as being a gas/gas reaction.

The preferred range for the amount of sorbed hydrocarbons withdrawn in the recirc stream from the MOD reactor will typically be greater than that withdrawn with the recirc stream from the MOG reactor, based on the same recirc rate. But the amount of the recirc stream withdrawn will preferably be in the range from about 0.05% to 10% per hour of the catalyst inventory in the MOD reactor.

The operation of the process with a MOD reactor is analogous to that of the MOG reactor except for the operating conditions. The MOD fluid bed is maintained at a temperature in the range from about 100°–350° C. (212°–662° F.) and a pressure in the range from about 2070–10335 kPa (300–1500 psig) in the absence of added hydrogen; WHSV in the range from about 0.1 to about 20 hr$^{-1}$, and preferably from 0.5 to 5 hr$^{-1}$, producing a MOD effluent containing a major amount of $C_{10}{}^+$ hydrocarbons essentially free of aromatics.

Operation with a fluid bed MOL reactor (Lubes Mode):

The MOL reactor is a fluid bed, operated in a manner analogous to that described hereinabove for the fluid bed MOD reactor, except that the pressures typically will be higher and the temperatures lower than those used in the MOD fluid bed. The ranges for the MOL reactor are set forth hereinbefore.

The preferred range for the flow rate of the recirc stream from the MOL reactor, and the amount of sorbed hydrocarbons withdrawn in the recirc stream, is typically in the same range as that set forth for the MOD reactor.

The bed of catalyst in a MOGDL reactor consists essentially of a finely divided medium pore zeolite metallosilicate catalyst having a constraint index in the range from 1 to 12, and a fresh catalyst activity (alpha) in the range from about 50 to 300. Lubes produced have viscosities in the range from about 10 cst (centistokes) at 40° C. to about 60 cst at 100° C., and more preferably in the range from about 19 cst at 40° C. to about 34 cst at 100° C.. Additional details relating to the catalyst are set forth in the Owen et al '779 patent, the disclosure of which is incorporated by reference thereto as if fully set forth herein.

Whichever the mode in which the MOGDL fluid bed reactor operates, it does so in combination with a purging lock-hopper, a stripper, both of which, in the best mode are replaced with a lock-stripper; a regenerator; a charging lock-hopper; and, assorted conventional complementary equipment, with conditions for each mode adapted to the process economics specifically applicable to the oligomerization reaction to be carried out in the reactor. The operation of the regenerator, however, is essentially independent of the conditions of operation of the reactor.

Figure 2:
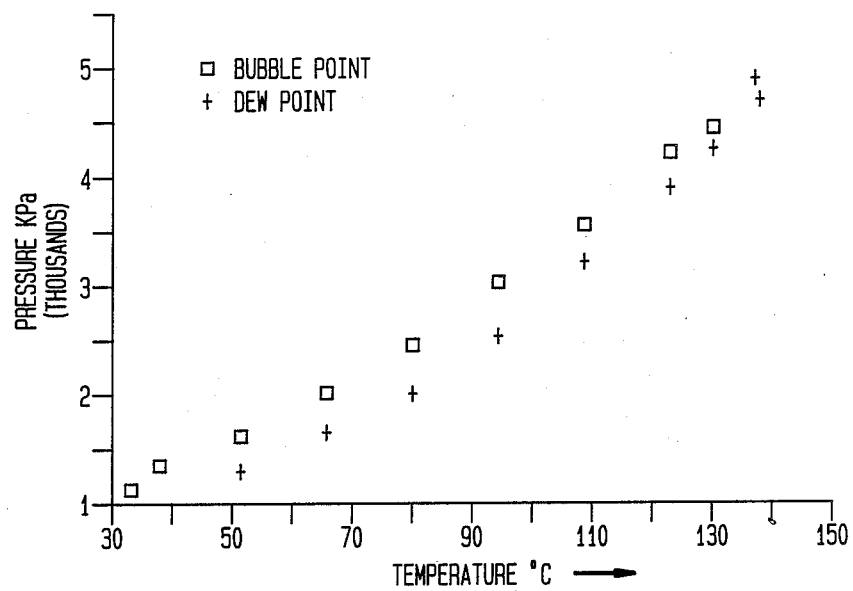
FIG. 2 is a phase diagram showing a plot of dew-point and bubble-point curves for a typical predominantly $C_3$-$C_4$ light gas feedstock to be upgraded.

Operation at or above $P_{max}$ and $T_{max}$ Referring now to FIG. 2 there is shown a plot of dew-point and bubble point curves of a typical light gas feed in a phase diagram for a range of temperatures from about 37.8° C. (100° F.) and about 689 kPa (100 psia), to the critical point, about 132° C. (270° F.) and 4272 kPa (620 psia), the light gas having the following composition:

| | |
|---|---|
| $C_3^=$ | 25.5% by wt. |
| $C_3$ | 7.6% |
| $C_4^=$ | 43.7% |
| $C_4$ | 23.2% |

It is evident from the phase diagram for the feed, that above about 965 kPa (140 psia) there is less than about 23° C. (50° F.) separating the gas and liquid phases. The difference in temperature becomes progressively smaller as the pressure increases, becoming zero at the critical point.

Figure 3:
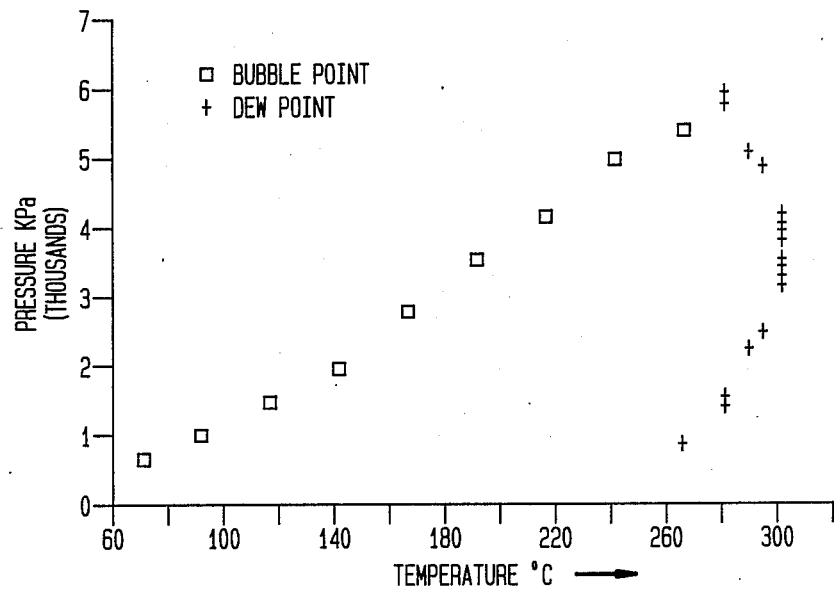
FIG. 3 is a phase diagram showing a plot of dew-point and bubble-point curves for a typical distillate range product produced in the effluent of a MOD reactor, from light gas feed.

Referring to FIG. 3, there is shown a phase diagram for a typical effluent produced in a MOD reactor. The phase diagram is over a temperature and pressure ranging from about 65.5° C. (150° F.) and about 1240 kPa (180 psia), to the critical point, which is at about 282° C. (540° F.) and 5994 kPA (870 psia).

It is evident from the phase diagram in FIG. 3 that the phase envelope has been expanded, relative to that for the feed (FIG. 2), and shifted towards higher temperatures. There is a much wider spread of temperature between the dew-point and bubble point curves at any given pressure except within about 689 kPa (100 psia) from $P_{cr}$. The difference in temperature becomes progressively smaller as the pressure increases, becoming zero at the critical point. The dewpoint curve for the product is more vertiginous than that for the feed, actually showing a convex bulge, indicating that a temperature above about 288° C. (550° F.) is favored.

In a fluid-bed MOD reactor, the conditions under which the single fluid bed operates to produce the foregoing distillate product is as follows:

| | |
|---|---|
| Temperature (inlet) | 204.4° C. (400° F.) |
| WHSV | 0.3 hr |
| Pressure (inlet) | 6787 kPa (985 psia) |

In a fluid bed MOL reactor, the pressure will generally be in excess of 6990 kPa (1000 psig) and the inlet temperature will be less than 300° C. (572° F.). Hydrogen may be introduced to the reactor, if desired, but is not necessary. It will be understood that the inlet temperature is typically lower than the bed temperature because the reaction exotherm raises the temperature, and heat transfer to the cooling coils in the bed is controlled to maintain the desired bed temperature.

Since operating conditions of the fluid bed are chosen so that no liquid is formed during the reaction, it is essential that not only the more expanded phase envelope (compared to the relatively narrow one for the feed) for the product be considered, but also all phase envelopes for the hydrocarbon intermediates formed during the reaction. The product contains heavier molecules made during the reaction, so that the phase envelope for the product is distinguishable over that for the feed in that the former is now relatively expanded, and shifted towards higher temperatures. When the desired product selectivity is obtained at a temperature above that corresponding to the dewpoint curve of the product, and above at least 204° C. (400° F.), the optimum (low) pressure may be used to minimize equipment cost. If the desired selectivity cannot be obtained at $T_{max}$, or a temperature just above it, then the operating pressure may need to be raised substantially above $P_{max}$. The combination of operating process conditions chosen will depend upon the particular specifications of product desired.

Operation of the Stripper:

The conditions for stripping the catalyst are preferably as low as is consistent with the cost of compressing stripped gas to be returned to the process. Typically the stripper is operated at substantially the same relatively low pressure in the range from atmospheric to about 50 psig, irrespective of the mode of operation of the MOGDL reactor. However, under certain circumstances, where the reactor operating pressure is sufficiently low, and an adequate supply of compressed stripping gas at sufficiently high pressure is available, the stripper may be operated at about reactor pressure. Thus, in some instances it may be beneficial to operate the stripper at relatively high pressure in the range from about 445-650 kPa (50-80 psig). In such an instance, particularly when the operating pressure of the stripper is greater than one-half the operating pressure of the reactor, stripping may be continuous.

The preferred stripper operating temperature is in the range from about 205°-371° C. (400°-700° F.) and the pressure in the range from about 240-445 kPa (20-50 psig). The operating pressure is relatively constant though it may vary within a narrow range on either side of the desired pressure. When the stripping medium is steam, the conditions of pressure and temperature are dictated by limits of the deactivation curve of the catalyst, above which curve the catalyst is unacceptably deactivated. The most preferred stripping conditions are chosen to provide the highest temperature and lowest economic pressure at which the catalyst will not be affected deleteriously. Steam pressure is typically 5–50 psig higher than the operating pressure of the stripper.

Operation of the Lock-Stripper:

Since the lock-stripper must first perform as a lock-hopper, then as a stripper, the lock-stripper operates under variable pressure. The initial pressure is high enough to provide a desirable pressure drop which permits flow from the reactor without excessive attrition of the catalyst through valve 29; then, after the valve is closed, the pressure is decreased to purge the purgable hydrocarbons in the recirc stream. The pressure is then decreased still further to strip as much of the remaining volatiles hydrocarbons (which are sorbed in the catalyst) as practical. The lock-stripper is pressurized with stripping gas before the recirc catalyst is allowed to flow into the lock-stripper from the reactor. Typically the pressure is high enough to avoid damaging the valve in the recirc line due to too high a velocity, though below sonic, of the recirc catalyst stream, and, as in all operations transferring catalyst from one process stage to another, a small enough pressure drop is maintained across an opened valve, to avoid unduly high attrition of the catalyst. Thereafter, the pressure is decreased, and the catalyst stripped in a manner analogous to that described for the stripper. Use of a "swing" lock-stripper allows continuous stripping without interrupting the flow of the recirc stream from the reactor.

Operation of the Regenerator:

The conditions for regenerating coked up catalyst are generally substantially the same irrespective of the mode of operation of the MOGDL reactor, and again, are dictated by the economics of operating the chosen process embodiment under pressure. The preferred regenerator operating temperature is in the range from about 427°–650° C. (800°–1200° F.) and the pressure in the range from about 240–445 kPa (20–50 psig). The regenerator may be operated continuously, though stripped catalyst is flowed to it only intermittently. If the 'coke make' and the rate of flow of recirc catalyst are each small enough, stripped catalyst may be accumulated in the regenerator until there is enough to regenerate it economically. Under appropriate conditions, the regenerator may thus be operated semi-continuously. Because of the process conditions under which the catalyst is stripped of hydrocarbons, and under which it is coked up, it may be activated by air alone, a flue gas recycle being unnecessary to doctor the air and keep the regenerator outside the explosive limits of its contents.

The MOGDL reactor is operable with shape selective medium pore catalysts exemplified by ZSM-5, ZSM-11, ZSM-12, ZSM-23, ZSM-35, ZSM-38, ZSM-48, zeolite beta, and other similar materials. U.S. Pat. No. 3,702,886 describing and claiming ZSM-5; U.S. Reisssue Pat. No. Re. 29,948 describing and claiming a crystalline material with an X-ray diffraction pattern of ZSM-5; and, U.S. Pat. No. 4,061,724 describing a high silica ZSM-5 referred to as "silicalite" are each incorporated by reference thereto as if fully set forth herein. Similarly, the disclosures relating to ZSM-11, ZSM-12, ZSM-23, ZSM-35, ZSM-38, and ZSM-48 set forth in U.S. Pat. Nos. 3,709,979, 3,832,449, 4,076,842, 4,016,245, 4,046,859, and 4,375,573, respectively, are each incorporated by reference thereto as if fully set forth herein.

In general the aluminosilicate zeolites are most effectively employed in our reactors. However, zeolites in which some other framework element which is isoelectronic to aluminum and which is present in partial or total substitution of aluminum can be advantageous. Illustrative of elements which can be substituted for art or all of the framework aluminum are boron, gallium, titanium, and, in general, any trivalent metal which is heavier than aluminum. Specific examples of such catalysts include ZSM-5 and zeolite Beta containing boron, gallium and/or titanium. In lieu of, or in addition to, being incorporated into the zeolite framework, these and other catalytically active elements can also be deposited upon the zeolite by any suitable procedure, e.g., by impregnation.

The aluminosilicates are preferred catalysts. These can be described as a three-dimensional framework of $SiO_4$ and $AlO_4$ tetrahedra in which the tetrahedra are cross-linked by the sharing of oxygen atoms whereby the ratio of total aluminum and silicon atoms to oxygen atoms is 1:2. In their hydrated form, the aluminosilicates may be represented by the formula:

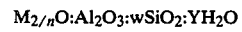

$$M_{2/n}O:Al_2O_3:wSiO_2:YH_2O$$

wherein M represents at least one cation which balances the electrovalence of the tetrahedra, n represents the valence of the cation, w the moles of $SiO_2O$ and Y the moles of $H_2$. The cations can be any or more of a number of metal ions, depending upon whether the aluminosilicate is synthesized or occurs naturally. Typical cations include sodium, lithium, potassium, silver, magnesium, calcium, zinc, barium, iron, nickel, cobalt and manganese. Although the proportions of inorganic oxides in the silicates and their spatial arrangements may vary affecting distinct properties in the aluminosilicate, the main characteristic of these materials is their ability to undergo dehydration without substantially affecting the $SiO_4$ and $AlO_4$ framework.

Aluminosilicates falling within the above formula are well known and, as noted, include synthesized aluminosilicates, natural aluminosilicates, and certain caustic treated clays. Among the aluminosilicates are included zeolites, Y, L, S, X, levynite, erionite, faujasite, analcite, paulingite, noselite, phillipsite, datolite, gmelinite, leucite, scapolite, mordenite as well as certain caustic treated clays such as montmorillonite and kaolin families. The preferred aluminosilicates are those having pore diameters of greater than about 6 Å (Angstroms).

Aluminosilicates may be treated with a fluid medium or media in a known manner to include a wide variety of aluminosilicates both natural and synthetic which have a crystalline, or, combination of crystalline and amorphous structure. These "promoters" may be provided in the catalyst by impregnation or ion exchange.

Though the process of the invention is operable with any of the aluminosilicates the preferred catalyst is a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within the zeolitic framework. These medium pore zeolites are favored for acid catalysis; however, the advantages of ZSM-5 type structures may be utilized by employing highly siliceous materials or crystalline metallosilicate having one or more tetrahedral species having varying degrees of acidity. The ZSM-5 crystalline structure is readily recognized by its X-ray diffraction pattern, which is described in U.S. Pat. No. 3,702,866 (Argauer, et al.), incorporated by reference herein.

The oligomerization catalysts preferred for use herein include the medium pore (i.e., about 5-7 Å) shape-selective crystalline aluminosilicate zeolites having a silica-to-alumina ratio of at least 12, a constraint index of about 1 to 12, preferred alpha during operation in the range from about 2 to about 15. In the MODL reactor the coked catalyst may have an apparent activity (alpha value) of about 2 to 25 under the process conditions to achieve the required selectivity and per pass conversion. Representative of the ZSM-5 type zeolites are ZSM-5, ZSM-11, ZSM-12, ZSM-22, ZSM-23, ZSM-35 and ZSM-38. Details about ZSM-5 are disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245; 4,046,839; 4,414,423; 4,417,086; 4,517,396 and 4,542,251, the disclosures of which are incorporated by reference thereto as if fully set forth herein. A typical zeolite catalyst component having Bronsted acid sites may consist essentially of aluminosilicate ZSM-5 zeolite with 5 to 95 wt % silica and/or alumina binder.

These siliceous zeolites may be employed in their acid forms, ion exchanged, or impregnated with one or more suitable metals, such as Ga, Pd, Zn, Ni, Co and/or other metals of Periodic Groups III to VIII. The zeolite may include a hydrogenationdehydrogenation component (sometimes referred to as a hydrogenation component) which is generally one or more metals of group IB, IIB, IIIB, VA, VIA or VIIIA of the Periodic Table (IUPAC), especially aromatization metals, such as Ga, Pd, etc. Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (eg, ionic $Ni^{+2}$, and a shape-selective medium pore acidic oligomerization catalyst, such as ZSM-5 zeolite) which components may be present in admixture or combined in a unitary bifunctional solid particle. It is possible to utilize an ethene dimerization metal or oligomerization agent to effectively convert feedstock ethene in a continuous reaction zone.

Certain of the ZSM-5 type medium pore shape selective catalysts are sometimes known as pentasils. In addition to the preferred aluminosilicates, the borosilicate, ferrosilicate and "silicalite" materials may be employed. It is advantageous to employ a standard ZSM-5, suitably modified, having a silica:alumina molar ratio in the range from 12:1 to 100:1, a constraint index in the range from 5 to 12, and with the aforesaid alpha value to convert substantially all the olefins in the feedstock.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02-1 micron being preferred, and an apparent crystal density in the range from about 0.6 to 1.9 $gm/cm^3$. In order to obtain the desired particle size for fluidization in the turbulent regime, the zeolite catalyst crystals are bound with a suitable inorganic oxide, such as silica, alumina, etc. to provide a zeolite concentration of about 5 to 95 wt %. In the description of preferred embodiments a 25% HZSM-5 catalyst contained within a silica-alumina matrix and having a fresh alpha value of about 80 is employed unless otherwise stated.

It is advantageous to employ a particle size range consisting essentially of 1 to 200 microns. Average particle size is usually about 20 to 100 microns, preferably 50 to 100 microns. The optimum particle size distribution is obtained with a mixture of larger and smaller particles within the above-specified range, having from 5-20% by weight fines. Close control of distribution is maintained with the fines in the size range less than 32 microns.

The average particle density of the catalyst as used may be tailored for optimum fluid-bed operation by compositing it with a matrix component of appropriate density. Such matrix components which provide particles of progressively increasing overall packed density are silica, alumina, beryllia, magnesia, barium oxide, zirconia, and titania, yielding values of from about 2.2 $gm/cm^3$ for silica, up to about 5.9 $gm/cm^3$ for zirconia. In our MODL reactor, the overall packed density of medium pore zeolite particles so composited, including the matrix component, can advantageously vary from about 0.6 to about 4 $gm/cm^3$, more preferably from about 2 to about 3 $gm/cm^3$.

Several useful parameters contribute to fluidization in the turbulent regime in accordance with the process of the present invention. When employing a ZSM-5 type zeolite catalyst in fine powder form such a catalyst should comprise the zeolite suitably bound or impregnated on a suitable support with a solid density (weight of a representative individual particle divided by its apparent "outside" volume) in the range from 0.6-2 g/cc, preferably 0.9-1.6 g/cc. When these solid particles are placed in a fluidized bed where the superficial fluid velocity is 0.06-0.5 m/s, operation in the turbulent regime is obtained. Those skilled in the art will appreciate that at higher pressures in the range, a lower gas velocity may be employed to ensure operation in the turbulent fluidization regime.

Referring again to FIG. 4, a more detailed description is now provided specifically for the gasoline mode of the gas-phase process (using a MOG reactor). It readily will be understood that the distillate and lubes embodiments will be operated in an analogous manner, but under different operating conditions.

A light-gas or naphtha feed, rich in $C_3$-$C_4$ olefins passes through conduit 10 when valve 33 is opened, into a charging lock-hopper 42, so termed because feed and catalyst (the "charge") are charged to MOG reaction vessel 20 from this lock-hopper. The charging lock-hopper is provided with a vent line 38 equipped with a vent valve 39 from which feed hydrocarbons, remaining after the charge is flowed into the reactor, may be vented. A porous sintered metal plate 48 may be provided in the upper portion of the lock-hopper to filter out catalyst. Make-up catalyst from catalyst hopper 11 is added through line 12 to regenerator 30. Regenerated catalyst is flowed into the charging lock-hopper 42 through conduit 46, provided with inlet valve 13, which also serves to control the flow from the regenerator. Inlet valve 13 and vent valve 39 are closed, as is outlet valve 14 while the charging lock-hopper is charged with feed to lift the catalyst charge into the MOG reaction vessel.

When there is a build-up of pressure, sufficient to maintain a desirable pressure differential between the charging lock-hopper 42 and the reaction vessel 20, the outlet valve 14 in conduit 49 is opened, and feed flowed through line 10, then line 49 using an appropriate conduit, preferably one which by-passes the charging lock-hopper, to carry the desired weight of catalyst and charge it to vessel 20 which is to operate preferably above about 550 kPa (65 psig). The regenerated catalyst is lifted codirectionally with the feed from a zone of higher pressure, into the reactor's catalyst bed, a zone of lower pressure, because the feed at the reactor's inlet is at a pressure higher than that at the outlet of the bed (taken at outlet of catalyst return riser conduit 50).

Simultaneously, feed may be flowed, with appropriate valving (not shown), into line 49 while the feed is flowed to the charging lock-hopper, to help lift the charge into the reactor. The particular valving for a desired sequence of steps for charging the catalyst will be determined by which steps one skilled in the art wishes to practice.

After charging the catalyst, the main feed is directed, with appropriate valving, through line 10' and bottom inlet line 15, for distribution through grid plate 22 into the fluidization zone 24 which is typically at a pressure in the range from about 790–1845 kPa (100–250 psig). The feed, at an inlet temperature in the range from about 38°–371° C. (100°–700° F.), typically 149°–204° C. (300°–400° F.), contacts the bed 24 of finely divided catalyst particles at a WHSV preferably in the range from about 0.2 to 2 hr$^{-1}$ which is sufficient to maintain the bed in the turbulent regime. MOG reactor 20 is provided with heat exchange tubes 26, which may be arranged as several separate heat exchange tube bundles so that temperature control can be separately exercised over different portions of the fluid catalyst bed. The bottoms of the tubes are spaced above feed distributor grid 22 sufficiently to be free of jet action by the charged feed through the small diameter holes in the grid. Alternatively, a substantial portion of the reaction heat can be removed by using cold feed. Baffles may be added to control radial and axial mixing. Although depicted without baffles, the vertical reaction zone can contain open end tubes above the grid for maintaining hydraulic constraints, as disclosed in U.S. Pat. No. 4,251,484 (Daviduk and Haddad). Heat released from the reaction may also be controlled by adjusting feed temperature in a known manner.

Catalyst outlet means 28 is provided for withdrawing catalyst from catalyst bed 24 via control valve 29 and codirectionally passing catalyst particles and entrained hydrocarbons into purging lock-hopper 41 which is a zone of lower pressure relative to that of the reactor. Typically, valves 45 and 47 are closed, and the lock-hopper 41 is pressurized with inert gas or steam through line 55', to at least one-half the outlet pressure of the reactor. When enough catalyst is withdrawn, consistent with a desired catalyst withdrawal rate, valve 29 is closed and valve 45 is gradually opened until the pressure in the lock-hopper approaches about 50 psig; the fall in temperature in the stripper is dictated by the drop in pressure. Sorbed hydrocarbons which are purged leave through line 43 and are combined with the effluent from the MOG reactor, which effluent leaves through line 56. The catalyst is separated from sorbed hydrocarbons by a sintered porous metal plate 48 in the top of the lock-hopper 41 when the purging lock-hopper is vented through line 43. The recovered hydrocarbons may be recycled to charging lock-hopper 42.

At the end of the purging cycle, after the hydrocarbons are purged from purging lock-hopper 41, the catalyst is flowed, via stripper inlet line 18 when valve 47 is opened, to stripper 51, operating at lower pressure than purging lock-hopper 41. The pressure in either the reactor or the stripper 51 is essentially unaffected during the transfer of catalyst from the purging lock-hopper. The pressure in the stripper is maintained low enough to strip the catalyst of essentially all remaining sorbed hydrocarbons which leave through line 53 when stripper outlet valve 59 is opened. Depending upon the catalyst temperature, and the particular catalyst's sensitivity to steam, the preferred stripping medium may be steam or nitrogen which is introduced near the bottom of the stripper through line 55. The pressure in the stripper, after stripping is completed, is about 35 psig, which is adequate to transfer the catalyst through line 58 to the regenerator 30. The pressure during stripping may be lower than 35 psig to facilitate stripping. In a manner analogous to that described for the lock-hoppers, a sintered porous metal plate 48 may be used in the upper portion of stripper 51.

As an alternative, the oligomerizable hydrocarbon effluents from the stripper and lock-hoppers may be combined, then flowed through a filter means (not shown) before the combined effluents are recycled to the process. The combined streams may be condensed and separated from the stripping medium. The liquefied hydrocarbons containing fines are recycled to the charging lock-hopper 42.

The stripped partially deactivated catalyst particles are entrained in a lift gas and transported via riser tube 32 to near the top of regenerator 30. The catalyst is oxidatively regenerated by controlled contact with air or other regeneration gas at an elevated temperature, preferably about 455° F. (850° F.) in a fluidized regeneration zone to remove carbonaceous deposits and restore catalyst activity. Air is distributed at the bottom of the bed to effect fluidization, with oxidation byproducts being carried out of the regeneration zone through cyclone separator 34, which returns any entrained solids to the bed. Flue gas from the top of the regenerator is withdrawn for disposal via conduit 36.

Regenerated catalyst is periodically flow-controlled into charging lock-hopper 42 through line 46 and its inlet valve 13, to complete the sequence of intermittently withdrawing a recirc stream containing used, coked up catalyst from the MOG reactor, purging the recirc stream, stripping the purged catalyst, regenerating the stripped catalyst, and charging the regenerated catalyst to the MOG reactor which is operated continuously. In the foregoing configuration, the MOG reactor and regenerator operate continuously, but the other operations are semicontinuous. They may be carried out continuously, if additional "swing" purging and charging lock-hoppers are used.

Since the amount of regenerated catalyst passed to the charging lock-hopper is relatively small, and the temperature difference between the reactor and regenerator not great, the temperature of the regenerated catalyst in the charge does not upset the temperature constraints of the reactor operations to a significant extent. A series of sequentially connected cyclone separators 52, 54 are provided with diplegs 52A, 54A to return any entrained catalyst fines to the lower bed. These separators are positioned in an upper portion of the reactor vessel containing dispersed catalyst phase 24. Filters, such as sintered metal plate filters, can be used alone or in conjunction with cyclones.

Under optimized process conditions, the turbulent bed has a superficial vapor velocity of about 0.1 to about 0.4 (m/sec). At higher velocities, entrainment of fine particles may become excessive and beyond about 2 m/sec the entire bed may be transported out of the reaction zone. Lower velocities than conventionally used are preferred because in a dense bed, the formation of detrimental large bubbles or gas voids is not a serious problem. However, fine particles are not maintained in a dense turbulent bed at a velocity over about 1 m/sec.

Figure 5:
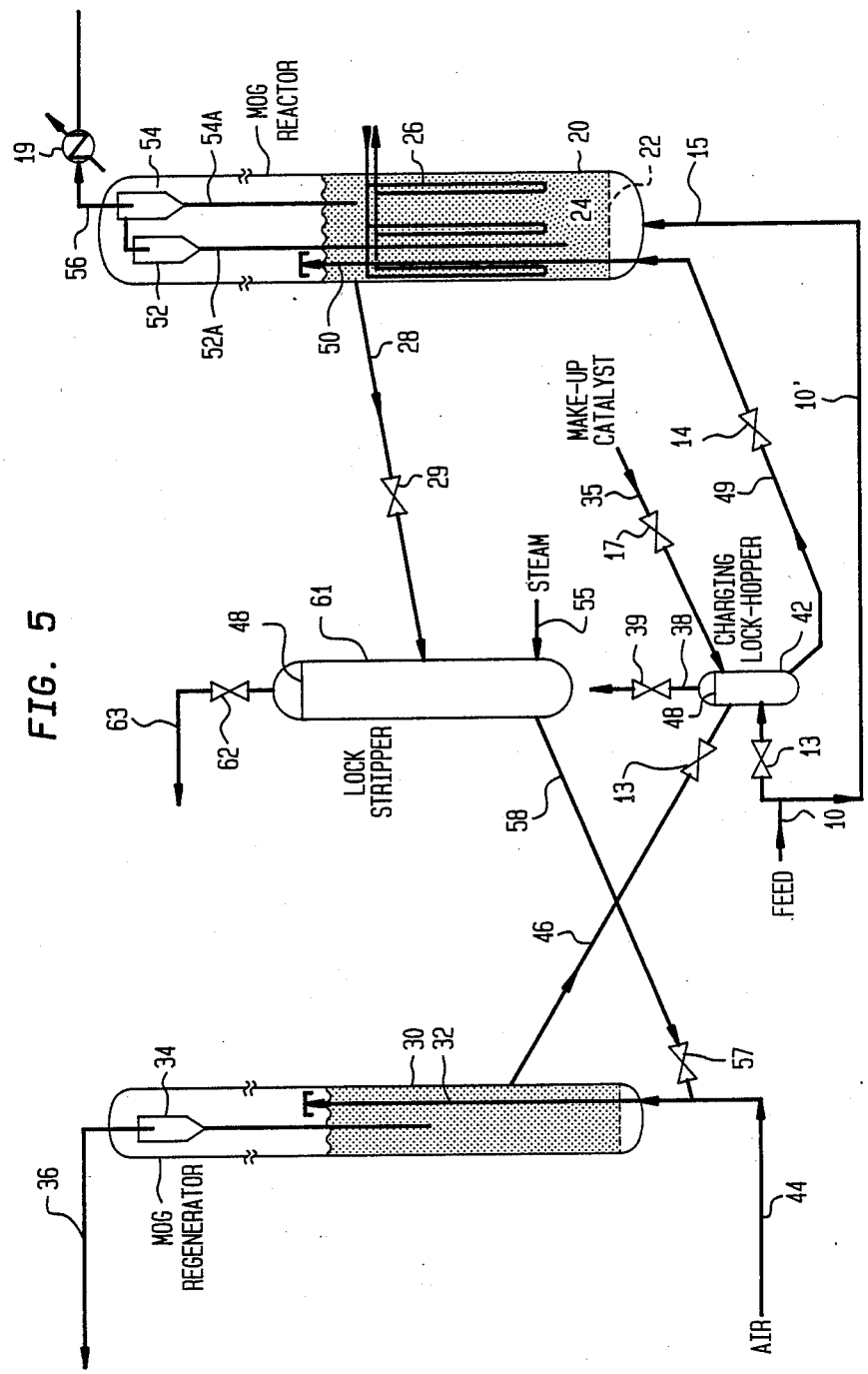
FIG. 5 is a flow diagram for another embodiment of the MOG process in which we use a lock-stripper to dispense with using a purging lock-hopper; and, because the amount of make-up catalyst required is typically small, we dispense with the make-up catalyst hopper, and charge make-up catalyst to the charging lock-hopper, intermittently, as needed.

Referring now to FIG. 5, there is illustrated a second embodiment of our process in which make-up catalyst is intermittently added to charging lock-hopper 42, after it is depressured, when valve 17 in line 35 is opened. After the valve 17 is closed, catalyst particles and feed are codirectionally charged to the MOG reactor, from the charging lock-hopper 42, as before.

Line 28 flows recirc catalyst directly to lock-stripper 61 which is a pressure-isolatable zone so that it also functions as a lock-hopper. Before receiving a charge of recirc catalyst, the lock-stripper 61 is pressurized with stripping gas through line 55, to a pressure high enough to counter and minimize the deleteriously high pressure drop and resulting sonic velocity to which valve 29 would otherwise be subjected when it is opened. This pressure is typically more than one-half the outlet pressure of the reactor. The lock-stripper operates under varying pressure when valve 57 is closed, the pressure ranging from a maximum when the lock-stripper is pressurized by the stripping medium, to a minimum, near the end of the stripping cycle when it is depressured. With a single lock-stripper, stripping is semicontinuous, but with the addition of a "swing" lock-stripper, stripping may be continuously effected, if desired.

The regenerator is operated continuously. Before the stripper is charged with recirc catalyst, the level of catalyst in the regenerator is built up to a maximum, and we continue drawing regenerated catalyst. To keep the regenerator hot during this period we may add fuel gas (or other source of heat), or use regenerating air which has been preheated to a sufficiently high temperature.

When the amount of catalyst in the lock-stripper (or stripper) is built up, valve 57 is opened to replenish the supply of recirc catalyst in the regenerator. The catalyst, directly flowed to the regenerator, can be lifted into the regenerator in combination with fluidizing air delivered through conduit 44.

If desired, with appropriate valving and conduits, one may simultaneously charge catalyst to the MOG reactor, and charge recirc catalyst to the regenerator.

In the first embodiment of our process, stripping and regeneration may proceed continuously with the use of swing purging lock-hoppers. In the second embodiment, an additional swing "lockstripper" allows continuous stripping and regenerating. There is no economic incentive for charging catalyst to the reactor continuously.

A typical preferred dense turbulent bed in a MOG reactor has an operating density of about 450 to 1000 kg/m$^3$, measured at the bottom of the reaction zone. Pressure differential between two vertically spaced points in the reactor volume may be measured to obtain the average bed density at such portion of the reaction zone. For instance, in a typical fluidized bed system employing HZSM-5 particles having an apparent packed density of 1000 kg/m$^3$ and real density of 2430 kg/m$^3$, an average fluidized bed density of about 450 to 800 kg/m$^3$ is satisfactory.

By virtue of the turbulence experienced in the turbulent regime, gas-solid contact in the catalytic reactor is improved, providing at least 80% conversion of $C_3$-$C_6$ alkenes, from 60% to about 95% selectivity, and temperature uniformity. One main advantage of this technique is the inherent control of bubble size and characteristic bubble lifetime. Bubbles of the gaseous reaction mixture are small, random and short-lived, thus resulting in such good contact between the gaseous reactants and the solid catalyst particles that typically, more than 90% of the butenes and about 94% of the propene is converted.

The hot gaseous MOG effluent, comprising mainly $C_5$+ olefins with some aromatics, paraffins and naphthenes, hydrogen and nitrogen, is separated from catalyst particles in the cyclone separating system 52, 54, and passes through line 56 to a condenser means 19 in which a minor amount by wt of the $C_5$-$C_9$ intermediate hydrocarbons, and substantially all the $C_{10}$+ is condensed and flowed for further processing.

The MOG reactor is designed as a pressure vessel required to contain a turbulent fluid-bed of catalyst desirably in the range from about 3–20 meters in height, preferably about 8 meters, and, operates at relatively low WHSV, preferably less than 10 hr$^{-1}$. Fine particles may be included in the bed, especially due to attrition, and the fines may be entrained in the product gas stream. A typical turbulent bed may have a catalyst carryover rate of about 1.5 times the reaction zone inventory per hour. If the fraction of fines becomes large, a portion of the carryover may be removed from the system and replaced by larger particles. It is desirable to have a fine particle separator such as a cyclone and/or filter means, disposed within or outside the reactor shell to recover catalyst carryover and return this fraction continuously to the bottom of the reaction zone for recirculation at a rate of about one catalyst inventory per hour. Optionally, fine particles carried from the reactor vessel entrained with effluent gas can be recovered by a sintered metal filter operating at the MOG reactor conditions.

The operation of the turbulent MOGD fluid bed in the dense phase produces a remarkably low coking rate, generally less than 0.1 wt % of the olefins in the feed, which low rate allows one to operate the bed without regeneration for a long period of time. In some instances periodic regeneration is the preferred mode of operation. The desired activity of the regenerated catalyst is to be maintained. If not regenerated, the coke content will gradually increase to about 15% by wt of the catalyst, at which point the run is desirably terminated.

The per pass conversion of lower olefins is at least 80%, typically better than 90%, and a selectivity to $C_5$+ olefins is at least 60%, and generally better than 80%. Because $C_4$− hydrocarbons in the MOG effluent are undesirable, the highest practical per pass conversion which can be obtained is dictated by the economics of operating the MOG reactor at a pressure below 250 psig. Typically, the ratio of $C_5$+ to $C_4^{31}$ range hydrocarbons is held in the narrow range of from about 5:1 to about 10:1.

The feed to a MOGDL reactor will preferably be preheated by the internal coils 26 through which liquid feed is pumped under sufficient pressure to provide a gaseous feed to the respective beds, and at a temperature not much lower than about 20° C. from the desired operating temperature in each bed. The MOGDL regenerator will typically operate in the range from about 371° C.–510° C. (700° F.–950° F.), and a portion of the flue gas from the regeneration zone will be cooled to a sufficiently low temperature in the range from about 35°–50° C. (95°–122° F.), so that, if desired, the cooled flue gas may be recycled to the regeneration zone, and the remainder discharged.

EXAMPLE 1

In this illustrative example, a 'made-up' feed of ethylene and propylene, instead of a typical light gas or lower olefinic $C_2$–$C_6$ feed, is used in a pilot plant operating in the gasoline mode, with a moderate pressure, relatively high severity MOG reactor. The MOG reactor is provided with a bed of medium pore HZSM-5 zeolite catalyst having a silica to alumina ratio of about 70, and the usual means for controlling fluidization of the bed in the turbulent regime. The bed has an equilibrated alpha of about 5. The light gas feedstream is a 50/50 mixture of essentially pure ethylene and propylene which mixture is brought into contact with the catalyst maintained as a dense phase in a turbulent fluid-bed at a pressure of 1270 kPa (170 psig). The inlet temperature of the feed is about 149° C. (300° F.), and the temperature of the bed is maintained at about 427° C. (800° F.) The feed is flowed through the reactor at a WHSV of about 0.8 $hr^{-1}$, and, hydrocarbons from the effluent product are recovered.

After operation for a period of time sufficient to deposit about 1% of coke on the catalyst, 8%/hr of the catalyst inventory in the MOG reactor is withdrawn as the recirc stream, to be purged in a purging lock-hopper where the pressure is decreased to 50 psig and the purged hydrocarbons recovered with the reactor effluent. The purged catalyst is then flowed to the stripper and stripped with nitrogen, in an amount just sufficient to strip the catalyst. From about 0.5 to 5 lb of nitrogen, and preferably from 1 lb to about 2 lb, are used per 100 lb of catalyst to be stripped The stripped hydrocarbons are recovered with the reactor effluent.

The stripped catalyst is flowed to the regenerator which operates at about 308 kPa (30 psig) and about 482° C. (900° F.), with enough oxygen to burn off the coke deposit. The regenerated catalyst is then flowed to the charging lock-hopper at about 25 psig, where it is subsequently pressurized to about 1410 kPa (190 psig) to charge the catalyst and feed to the reactor.

The average of several analyses of reactor effluent recovered in each of the runs, for a single pass, indicates about 95% conversion of olefins with product selectivities presented in Table I below.

EXAMPLE 2

In a manner analogous to that described in example 1 hereinabove, a 'made-up' feed of 75% by wt propylene and 25% by wt ethylene is used in the same pilot plant as in example 1, again operating in the gasoline mode, under substantially the same process conditions as those set forth in example 1. The same recirc rate of catalyst is maintained, as are the stripping conditions.

The average of several analyses of reactor effluent recovered in each of the runs, for a single pass, indicates about 95% conversion of olefins with product selectivities presented in Table I below.

TABLE I

| | | Product Selectivity of Converted Olefins, % by wt | |
|---|---|---|---|
| Feed | | Ex. 1 50/50 $C_2^=/C_3^=$ | Ex. 2 75/25 $C_3^=/C_2^=$ |
| Effulent | $C_2^-$ | 3.2 | 2.0 |
| | $C_3$ | 12.7 | 10.3 |
| | $C_4$ | 23.9 | 22.6 |
| | $C_5^+$ | 59.9 | 64.8 |

The process coke make is found to be about 0.3 wt% of the feed.

In a manner analogous to that described hereinabove, a fluid bed reactor may be operated in the super-dense phase under conditions specified for such operation hereinbefore. A desirable recirc rate is established for regeneration of catalyst after a predetermined level of coke has built up during operation, and the recirc stream is purged and stripped before it is regenerated.

Having thus provided a general discussion, and a specific illustration of the best mode of operation of a single zone, dense, and super-dense turbulent fluid beds, and described the oligomerization of a monomeric predominantly olefinic light gas feedstream in such beds, it is to be understood that no undue restrictions are to be imposed by reason thereof, except as provided by the following claims.

We claim:

1. In a catalytic process for upgrading a light gas or light naphtha $C_2^+$ olefin-containing feedstream to a heavier product stream rich in $C_5^+$ aliphatic hydrocarbons said process comprising, contacting said olefin feedstream with a finely divided medium pore zeolite metallosilicate catalyst having a silica:alumina ratio greater than 12, and a constrain index in the range from about 1 to about 12, said catalyst maintained as a turbulent fluid-bed, flowing said olefin feedstream through said bed at a weight hourly space velocity (WHSV) in the range from about 0.1 to 20 $hr^{-1}$, without forming a liquid phase in said bed, maintaining a catalyst fines content of from about 5% to about 20% by wt, based on the weight of the catalyst in the bed, said fines having a particle size less than 32 microns, and, recovering said $C_5^+$ aliphatic hydrocarbons from said product stream leaving said bed, the improvement comprising:

(a) withdrawing less than 30 percent by weight of reactor catalyst per hour in a recirculated catalyst stream from an oligomerization zone in which said catalyst is fluidized by hydrocarbons in a non-liquid phase at above about 515 kPa (60 psig), said catalyst having less than 1% by weight of coke deposited on it (based on the weight/hr of olefins fed), and has said hydrocarbons sorbed in its voids and pores;

(b) confining said recirculated stream in a pressure-isolatable purging zone and depressuring it to below the operating pressure of said bed, to purge a major proportion by weight of said non-liquid hydrocarbons in said recirculated stream;

(c) transferring purged catalyst from said purging zone to a stripping zone;

(d) stripping said purged catalyst with a stripping medium under sufficiently low pressure to remove substantially all said hydrocarbons from said catalyst, and at a temperature at which said purged catalyst is not deleteriously affected, to produce a stripped catalyst;

(e) oxidatively regenerating the stripped catalyst to produce a regenerated catalyst essentially free of deposited coke; and, (f) returning said regenerated catalyst to the oligomerization zone via a pressure-isolatable charging zone, pressurizable to a pressure greater than the operating pressure of the oligomerization zone, whereby regeneration of said recirculated catalyst enables said reactor to maintain less than 1% by weight (based on the weight/hr of olefins fed), of coke deposited on the catalyst, and upgrade said feed to said $C_5+$ aliphatic hydrocarbons continuously.

2. The process of claim 1 wherein said fluid-bed operates under oligomerization conditions to product a predominantly gasoline range hydrocarbon produce at subcritical pressure above about 550 kPa (65 psig) and temperature above about 204° C, (400° F.), and said regenerator operates at a pressure above 100 kPA (14.7 psia) but below about 445 kPa (50 psig).

3. The process of claim 1 wherein said fluid-bed operates under oligomerization conditions to produce a predominantly 'heavies' distal late consisting essentially of distillate having a boiling point in the range from about 138° C. to about 349° C. (280° F.-660° F.), lubes range hydrocarbon product, and mixtures thereof, under super-dense conditions such that $P_{max}$ and $T_{max}$ lie outside a pressure and temperature region at which no liquid hydrocarbon phase is present, circumscribed by an arc having a radius corresponding to about a 344.5 kPa (50 psi) differential from the critical pressure and temperature point $P_{cr}$, $T_{cr}$, of hydrocarbons present as a mixture in said bed, said region being bounded by that portion of the bubble-point/dew-point curve which is downwardly inclined from said point; and, said catalyst is regenerated with an oxygen-containing gas in an amount sufficient to regenerate said stripped catalyst at a temperature in the range from above about 371° C. (700° F.) but below a temperature deleterious to said catalyst.

4. The process of claim 2 wherein said fluid-bed operates in the gasoline mode at a bed density, measured at the bottom of the reaction zone, greater than 300 kg/m³, a temperature in the range from about 315° C. (600° F.) to about 482° C. (900° F.).

5. The process of claim 3 wherein said bed operates in the 'heavies' mode at a bed density, measured at the bottom of the reaction zone, less than 850 kg/cm³, a temperature in the range from about 204° C. (400° F.) to about 371° C. (700° F.), and a pressure in the range from about 2857 kPa (400 psig) to about 13880 kPa (2000 psig).

6. The process of claim 1 wherein said catalyst is a shape selective medium pore siliceous metallosilicate acid zeolite having a constraint index in the range from 2 to about 12, an equilibarated alpha in the range from 2 to about 50, and said silica:alumina ratio is in the range from about 12:1 to about 70:1.

7. The process of claim 5 wherein said fluid bed is maintained in a reactor operated in a distillate mode a pressure in the range from about 2857 kPa to about 10436 kPa (400 psig-1500 psig), and a temperature in the range from 204° C. to about 371° C. (400° F.-700 ° F.).

8. The process of claim 5 wherein said fluid bed is maintained in a reactor operated in a lubes mode at a pressure in the range from about 270 kPa to about 13881 kPa (500 psig-2000 psig), and a temperature in the range from 204° C. to about 315° C. (400° F.-600° F.); and, said heavies consist essentially of lubes having a viscosity in the range from about 10 cst measured at 40° C. to about 60 cst measured at 100° C.

9. The process of claim 1 wherein said feedstream is essentially free of molecular hydrogen.

10. In a catalytic process for upgrading a light gas or light naphtha $C_2+$ olefin-containing feedstream to a heavier product stream rich in $C_5+$ aliphatic hydrocarbons said process comprising, contacting said olefin feedstream with a finely divided medium pore zeolite metallosilicate catalyst having a silica:alumina ratio greater than 12, and a constraint index in the range from about 1 to about 12, said catalyst maintained as a turbulent fluid-bed, flowing said olefin feedstream through said bed at a weight hourly space velocity (WHSV) in the range from about 0.1 to 20 $hr^{-1}$, without forming a liquid phase in said bed, maintaining a catalyst fines content of from about 5% to about 20% by wt, based on the weight of the catalyst in the bed, said fines having a particle size less than 32 microns, and, recovering said $C_5+$ aliphatic hydrocarbons from said product stream leaving said bed, the improvement comprising:

(a) withdrawing less than 30 percent by weight of reactor catalyst per hour in a recirculated catalyst stream from an oligomerization zone in which said catalyst is fluidized by hydrocarbons in a non-liquid phase at above about 515 kPa (60 psig), said catalyst has less than 1% by weight of coke deposited on it (based on the weight/hr of olefins fed), and has said hydrocarbons sorbed in its voids and pores;

(b) pressurizing a pressure-isolatable lock-hopper stripping zone with a stripping medium until a pressure is reached which is high enough to avoid deleterious attrition of catalyst in said recirculated stream;

(c) flowing said recirculated stream to said pressure-isolatable lock-hopper stripping zone at sufficiently velocity to avoid deleterious attrition of said catalyst;

(d) depressuring said lock-hopper stripping zone to below the operating pressure of said bed, so as to strip essentially all of said non-liquid hydrocarbons from said recirculated stream at a temperature at which said catalyst is not deleteriously affected, to produce a stripped catalyst;

(e) oxidatively regenerating said stripped catalyst to produce a regenerated catalyst essentially free of deposited coke; and, (f) returning said regenerated catalyst to the oligomerization zone via a pressure-isolatable charging zone, pressurizable to a pressure greater than the operating pressure of the oligomerization zone, whereby continuous operation of said reactor and said regenerator is maintained, enabling said reactor to maintain less than 1% by weight (based on the weight/hr of olefins fed), of coke deposited on the catalyst, and to upgrade said feed to said $C_5+$ aliphatic hydrocarbons continuously, and enabling said regenerator to operate essentially independently from said reactor.

11. The process of claim 10 wherein said fluid-bed operates under oligomerization conditions to produce a predominantly gasoline range hydrocarbons product at subcritical pressure above about 650 kPa (80 psig) and temperature above about 204° C. (400° F.), and said regenerator operates at a pressure above 100 kPa (14.7 psia) but below about 445 kPa (50 psig).

12. The process of claim 10 wherein said fluid-bed operates under oligomerization conditions to produce a predominantly 'heavies' distillate consisting essentially of distillate having a boiling point in the range from about 138° C. to about 349° C. (280° F.–660° F.), lubes range hydrocarbon product, and mixtures thereof, under super-dense conditions such that $P_{max}$ and $T_{max}$ lie outside a pressure and temperature region at which no liquid hydrogen phase is present, circumscribed by an arc having a radius corresponding to about a 344.5 kPa (50 psi) differential from the critical pressure and temperature point $P_{cr}$, $T_{cr}$, of hydrocarbons present as a mixture in said bed, said region being bounded by that portion of the bubble-point/dew-point curve which is downwardly inclined from said point; and, said catalyst is regenerated with an oxygen-containing gas in an amount sufficient to regenerate said stripped catalyst at a temperature in the range from above about 371° C. (700° F.) but below a temperature deleterious to said catalyst.

13. The process of claim 11 wherein said bed operates in the gasoline mode at a bed density, measured at the bottom of the reaction zone, greater than 300 kg/m$^3$, a temperature in the range from about 315° C. (600° F.) to about 482° C. (900° F.), and a pressure in the range from about 965 kPa (125 psig) to about 2860 kPa (400 psig).

14. The process of claim 12 wherein said bed operates in the 'heavies' mode at a bed density, measured at the bottom of the reaction zone, less than 500 kg/m$^3$, a temperature in the range from about 204° C. (400 ° F.) to about 371° C. (700° F.), and a pressure in the range from about 2857 kPa (400 psig) to about 13880 kPa (2000 psig) to produce said 'heavies' distillate.

15. The process of claim 10 wherein said catalyst is a shape selective medium pore siliceous metallosilicate acid zeolite having a constraint index in the range from 2 to about 12, an equalibrated alpha in the range from 2 to about 50, and said silica:alumina ratio is in the range from about 12:1 to about 70:1.

16. The process of claim 14 wherein said fluid bed is maintained in a reactor operated in a distillate mode at a pressure in the range from about 2857 kPa to about 10436 kPa (400 psig-1500 psig), and a temperature in the range from 204° C. to about 371° C. (400° F.–700° F.); and, said heavies consist essentially of distillate boiling point in the range from about 138° C. to about 349° C. (280° F.–660° F.).

17. The process of claim 14 wherein said fluid bed is maintained in a reactor operated in a lubes mode at a pressure in the range from about 5270 kPa to about 13881 kPa (500 psig-2000 psig), and a temperature in the range from 204° C. to about 315° C. (400° F.–600° F.); and, said heavies consist essentially of lubes having a viscosity in the range from about 10 cst measured at 40° C., to about 60 cst measured at 100° C.

18. The process of claim 10 wherein said feedstream is essentially free of hydrogen.

19. In a process for the continuous conversion of a light gas or light naphtha feedstock to heavier hydrocarbon products wherein the feedstock is contacted with a hydrocarbon fluidized bed of zeolite catalyst in a reaction zone at above about 550 kPa (65 psig), under oligomerization conversion conditions, a portion of coked catalyst from the bed is withdrawn, and is oxidatively regenerated, then returned to the bed at a rate sufficient to maintain a reaction severity index expressed as the propane:propene weight ratio in the hydrocarbon product at about 0.2:1 to 5:1, the improvement consisting essentially of:

(a) withdrawing from an oligomerization zone less than 30 percent by weight of catalyst in the bed per hour for a recirculated catalyst stream of codirectionally flowing catalyst particles, and, hydrocarbons in a non-liquid phase, said catalyst having less than 1% by weight of coke deposited on it (based on the weight/hr of olefins fed), and hydrocarbons sorbed in its voids and pores;

(b) transferring said recirculated stream to a pressure-isolatable pressurized lock-hopper stripping zone with a stripping medium until a pressure is reached which is high enough to avoid flow at sonic velocity of said stripping medium, and depressuring said lock-hopper stripping zone to below the operating pressure of said bed so as to purge a major proportion by weight of said non-liquid hydrocarbons in said recirculated stream without substantially affecting the pressure of the reactor;

(c) transferring stripped catalyst to a regeneration zone and oxidatively regenerating the stripped catalyst therein to produce a regenerated catalyst essentially free of deposited coke; and, (d) returning said regenerated catalyst to the oligomerization zone via a pressure-isolatable charging zone, pressurizable to a pressure greater than the operating pressure of the oligomerization zone, whereby regeneration of said recirculated catalyst in said amount enables said reactor to maintain a low level of coke formation on the catalyst, and upgrade said feed to said $C_5+$ aliphatic hydrocarbons continuously with at least 80% conversion of $C_3$–$C_6$ alkenes in the feedstock and from about 60% to about 95% selectivity.

20. The process of claim 19 wherein said fluid-bed operates under oligomerization conditions to produce a predominantly gasoline range hydrocarbon product at subcritical pressure above about 650 kPa (80 psig) and temperature above about 204° C. (400° F.), and said regenerator operates at a pressure above 100 kPa (14.7 psia) but below about 445 kPa (50 psig).

21. The process of claim 19 wherein said fluid-bed operates under oligomerization conditions to produce a predominantly 'heavies' distillate consisting essentially of distillate having a boiling point in the range from about 138° C. to about 349° C. (280° F.–660° F.), lubes range hydrocarbon product, and mixtures thereof, under super-dense conditions such that $P_{max}$ and $T_{max}$ lie outside a pressure and temperature region at which no liquid hydrocarbon phase is present, circumscribed by an arc having a radius corresponding to about a 344.5 kPa (50 psi) differential from the critical pressure and temperature point $P_{cr}$, $T_{cr}$, of hydrocarbons present as a mixture in said bed, said region being bounded by that portion of the bubble-point/dew-point curve which is downwardly inclined from said point; and, said catalyst is regenerated with an oxygen-containing gas in an amount sufficient to regenerate said stripped catalyst at a temperature in the range from above about 371° C. (700° F.) but below a temperature deleterious to said catalyst.

* * * * *

UNITED STATES PATENT AND TRADEMARK OFFICE
CERTIFICATE OF CORRECTION

PATENT NO. : 4,939,314

DATED : July 3, 1990

INVENTOR(S) : Harandi and Owen

It is certified that error appears in the above-identified patent and that said Letters Patent is hereby corrected as shown below:

Column 24, line 36, "constrain" should read --constraint--
Column 25, line 18, "product" should read --produce--
Column 25, line 26, "distal late" should read --distillate--
Column 25, line 52, "kg/cm$^3$" should read --kg/m$^3$--

Column 25, line 60, "equilibarated" should read --equilibrated--

Column 26, line 3, "270" should read --5270--
Column 26, line 10, delete "molecular"
Column 28, line 1, delete "hydrocarbon" and insert --turbulent--

Signed and Sealed this

Fourteenth Day of July, 1992

Attest:

DOUGLAS B. COMER

Attesting Officer

Acting Commissioner of Patents and Trademarks